(12) United States Patent
Spurk et al.

(10) Patent No.: US 10,316,739 B2
(45) Date of Patent: *Jun. 11, 2019

(54) METHOD AND DEVICE FOR THE PURIFICATION OF DIESEL EXHAUST GASES

(71) Applicant: UMICORE AG & Co. KG, Hanau-Wolfgang (DE)

(72) Inventors: Paul Spurk, Weiterstadt (DE); Marcus Pfeifer, Solingen (DE); Hendrik-David Noack, Hanau (DE)

(73) Assignee: UMICORE AG & CO. KG, Hanau-Wolfgang (DE)

(*) Notice: Subject to any disclaimer, the term of this patent is extended or adjusted under 35 U.S.C. 154(b) by 0 days.

This patent is subject to a terminal disclaimer.

(21) Appl. No.: 15/981,588

(22) Filed: May 16, 2018

(65) Prior Publication Data

US 2018/0258839 A1    Sep. 13, 2018

Related U.S. Application Data

(63) Continuation of application No. 13/000,927, filed as application No. PCT/EP2009/004543 on Jun. 24, 2009, now Pat. No. 10,001,053.

(30) Foreign Application Priority Data

Jun. 27, 2008  (EP) ..................... 08011654

(51) Int. Cl.
  *F01N 3/00*   (2006.01)
  *F02B 37/02*  (2006.01)
  (Continued)

(52) U.S. Cl.
  CPC .......... *F02B 37/02* (2013.01); *B01D 53/9477* (2013.01); *F01N 3/021* (2013.01);
  (Continued)

(58) Field of Classification Search
  CPC ........ B01D 53/9477; B01D 2251/2067; B01D 2255/1021; B01D 2255/1023;
  (Continued)

(56) References Cited

U.S. PATENT DOCUMENTS 4,961,917 A   10/1990  Byrne
5,021,227 A    6/1991  Kobayashi et al.
(Continued)

FOREIGN PATENT DOCUMENTS

DE            3635284       4/1988
DE     10 2004 013 165     10/2005
(Continued)

OTHER PUBLICATIONS

International Search Report for PCT/EP2009/004543 dated Oct. 23, 2009.
(Continued)

*Primary Examiner* — Audrey K Bradley
*Assistant Examiner* — Anthony Ayala Delgado
(74) *Attorney, Agent, or Firm* — Smith, Gambrell & Russell, LLP

(57) ABSTRACT

The invention proposes a method for the purification of exhaust gases which are generated by a diesel engine with a charging turbine, and a special device for carrying out said method. The device comprises, in the flow direction of the exhaust gas, a dosing device for a reducing agent from a reducing agent reservoir (2), an SCR catalytic converter (3), an oxidation catalytic converter (4) and a diesel particle filter (5). The system is particularly suitable for the purification of the exhaust gases of diesel vehicles in which engines with a turbocharger (charging turbine (1)) and an exhaust-gas recirculation device are used, which engines generate exhaust
(Continued)

gases which, in addition to carbon monoxide, hydrocarbons and particles, have nitrogen oxides with an $NO_2/NO_X$ ratio of between 0.3 and 0.7.

13 Claims, 4 Drawing Sheets

(51) Int. Cl.
| | |
|---|---|
| B01D 53/94 | (2006.01) |
| F01N 3/021 | (2006.01) |
| F01N 3/023 | (2006.01) |
| F01N 3/025 | (2006.01) |
| F01N 3/035 | (2006.01) |
| F01N 3/20 | (2006.01) |
| F01N 3/28 | (2006.01) |
| F01N 9/00 | (2006.01) |
| F01N 13/00 | (2010.01) |
| B01J 23/44 | (2006.01) |
| B01J 29/68 | (2006.01) |
| B01J 35/00 | (2006.01) |

(52) U.S. Cl.
CPC ........... *F01N 3/025* (2013.01); *F01N 3/0231* (2013.01); *F01N 3/035* (2013.01); *F01N 3/2006* (2013.01); *F01N 3/2066* (2013.01); *F01N 3/2882* (2013.01); *F01N 9/002* (2013.01); *F01N 13/0093* (2014.06); *F01N 13/0097* (2014.06); *B01D 53/944* (2013.01); *B01D 53/9418* (2013.01); *B01D 2251/2067* (2013.01); *B01D 2255/1021* (2013.01); *B01D 2255/1023* (2013.01); *B01D 2255/50* (2013.01); *B01D 2257/404* (2013.01); *B01D 2257/502* (2013.01); *B01D 2257/702* (2013.01); *B01D 2258/012* (2013.01); *B01J 23/44* (2013.01); *B01J 29/68* (2013.01); *B01J 35/0006* (2013.01); *F01N 2250/02* (2013.01); *F01N 2370/04* (2013.01); *F01N 2510/06* (2013.01); *F01N 2570/14* (2013.01); *F01N 2610/02* (2013.01); *F01N 2610/03* (2013.01); *Y02A 50/2325* (2018.01); *Y02A 50/2341* (2018.01); *Y02A 50/2344* (2018.01); *Y02T 10/144* (2013.01); *Y02T 10/24* (2013.01); *Y02T 10/26* (2013.01); *Y02T 10/47* (2013.01)

(58) Field of Classification Search
CPC .......... B01D 2255/50; B01D 2257/404; B01D 2258/012; B01D 53/9418; B01J 23/44; B01J 29/68; B01J 35/0006; F01N 2370/04; F01N 2610/02; F01N 3/2066
See application file for complete search history.

(56) References Cited

U.S. PATENT DOCUMENTS

| | | | |
|---|---|---|---|
| 5,059,569 | A | 10/1991 | Deschamps et al. |
| 5,116,579 | A | 5/1992 | Kobayashi et al. |
| 5,863,508 | A | 1/1999 | Lachman et al. |
| 5,968,464 | A | 10/1999 | Peter-Hoblyn et al. |
| 6,615,580 | B1 | 9/2003 | Khair |
| 6,689,709 | B1 | 2/2004 | Tran |
| 6,805,849 | B1 | 10/2004 | Andreasson et al. |
| 6,823,660 | B2 | 11/2004 | Minami |
| 6,928,806 | B2 | 8/2005 | Tennison et al. |
| 7,141,226 | B2 | 11/2006 | Twigg |
| 7,481,983 | B2 | 1/2009 | Patchett et al. |
| 7,498,010 | B2 | 3/2009 | Andreasson et al. |
| 7,601,662 | B2 | 10/2009 | Bull et al. |
| 7,971,430 | B2 | 7/2011 | Lambert |
| 8,065,870 | B2 | 11/2011 | Jobson et al. |
| 2003/0114300 | A1 | 6/2003 | Twigg |
| 2004/0098973 | A1 | 5/2004 | Tennison et al. |
| 2005/0138916 | A1 | 6/2005 | Bonadies et al. |
| 2005/0180905 | A1 | 8/2005 | Cichanowicz |
| 2005/0201916 | A1 | 9/2005 | Yavuz et al. |
| 2006/0029535 | A1 | 2/2006 | Ott |
| 2006/0193757 | A1 | 8/2006 | Li et al. |
| 2006/0213187 | A1 | 9/2006 | Kupe et al. |
| 2007/0044456 | A1 | 3/2007 | Upadhyay et al. |
| 2007/0081934 | A1 | 4/2007 | Hubig et al. |
| 2008/0045405 | A1 | 2/2008 | Beutel et al. |
| 2008/0060351 | A1 | 3/2008 | Pawson et al. |
| 2008/0127638 | A1 | 6/2008 | Vaarkamp et al. |
| 2008/0202096 | A1 | 8/2008 | Driscoll |
| 2008/0202107 | A1 | 8/2008 | Boorse et al. |
| 2008/0241060 | A1 | 10/2008 | Li et al. |
| 2008/0264036 | A1 | 10/2008 | Bellovary |
| 2009/0035194 | A1* | 2/2009 | Robel ............... F01N 3/0231 422/177 |
| 2009/0137386 | A1 | 5/2009 | Pfeifer et al. |
| 2009/0169451 | A1 | 7/2009 | Andreasson et al. |
| 2009/0205324 | A1 | 8/2009 | Girard et al. |
| 2010/0034717 | A1 | 2/2010 | Adelmann et al. |
| 2010/0077738 | A1 | 4/2010 | Cavataio et al. |
| 2010/0290963 | A1 | 11/2010 | Andersen et al. |
| 2011/0056187 | A1 | 3/2011 | Seyler et al. |
| 2011/0286903 | A1 | 11/2011 | Andreasson et al. |

FOREIGN PATENT DOCUMENTS

| | | |
|---|---|---|
| EP | 0 141 917 | 5/1985 |
| EP | 0 311 758 | 4/1989 |
| EP | 0 381 236 | 8/1990 |
| EP | 0 385 164 | 9/1990 |
| EP | 1 054 722 | 11/2000 |
| EP | 1 072 763 | 1/2001 |
| EP | 1 250 952 | 10/2002 |
| EP | 1 255 918 | 11/2002 |
| GB | 1 393 053 | 5/1975 |
| JP | 63-051948 | 3/1988 |
| JP | 1-130735 A | 5/1989 |
| JP | 2-4921 U | 1/1990 |
| JP | H05-212248 | 8/1993 |
| JP | 7-136513 A | 5/1995 |
| JP | 2000-185323 | 7/2000 |
| JP | 2001-239133 A | 9/2001 |
| JP | 2003-532012 | 10/2003 |
| JP | 2005-61362 A | 3/2005 |
| JP | 2005-264868 A | 9/2005 |
| JP | 2008-69727 A | 3/2008 |
| WO | 97/36676 | 10/1997 |
| WO | 98/28070 | 7/1998 |
| WO | 99/39809 | 8/1999 |
| WO | 2000/072965 | 12/2000 |
| WO | 2005/025725 | 3/2005 |
| WO | 2006/021337 | 3/2006 |
| WO | 2007/004774 | 1/2007 |
| WO | 2007/069994 | 6/2007 |
| WO | 2008/049491 | 5/2008 |
| WO | 2008/070551 A2 | 6/2008 |
| WO | 2008/118434 | 10/2008 |
| WO | 2008/132452 | 11/2008 |

OTHER PUBLICATIONS

English translation of a Notification of Reasons for Refusal for JP Appl. No. 2011-515198 having a "dispatch date" of May 20, 2013 (8 pages).
Internal Reconsideration Report for JP 2011-0515198, dated May 7, 2015; 3 Pages (English translation).
Ch. Baerlocher, et al., "Atlas of Zeolite Framework Types", 5$^{th}$ revised edition, 2001, ISBN: 0-444-50701-9, pp. 1-303.
W.M. Meier, "Zeolites and zeolite-like materials", Pure & Appl. Chem., 1986, vol. 58, No. 10 pp. 1323-1328.
Kou Sugawara, et al., "The importance of Fe loading on the $N_2O$ reduction with $NH_3$ over Fe-MFI: Effect of acid site formation on Fe

(56) References Cited

OTHER PUBLICATIONS species", Applied Catalysis B: Environmental, vol. 69, 2007, pp. 154-163.
W. Arous, et al., "Selective catalytic reduction of NO by $NH_3$ on Cu (II) ion-exchanged offretite prepared by different methods", Topics, Catalysis, 2007, vols. 42-43, pp. 51-54.
Tatsumi Ishihara, et al., "Copper Ion Exchanged SAPO-34 as a Thermostable Catalyst for Selective Reduction of NO with $C_3H_6$", Journal of Catalysis, 1997, vol. 169, pp. 93-102.
T. Mayer, "Feststoff-SCR-System auf Bases von Ammoniumcarbamat (Solid-state SCR system based on ammonium carbamate)", Thesis, Technical Universit Kaiserslautern, 2005.
G. Tuenter, et al., "Kinetics and Mechanism of the $NO_x$ Reduction with $NH_3$ on $V_2O_5$-$WO_3$-$TiO_2$ Catalyst", Ind. Eng. Chem, Prod. Res. Dev, 1986, vol. 25, pp. 633-636.
Korean Office Action dated Apr. 14, 2016 in Korean Patent Application No. 10-2016-7004921, 7 pages (and English translation).

\* cited by examiner

METHOD AND DEVICE FOR THE PURIFICATION OF DIESEL EXHAUST GASES

FIELD OF THE INVENTION

The invention relates to a method for the purification of exhaust gases which are generated by a diesel engine with a charging turbine, and to a special device for carrying out said method, which device comprises, in the flow direction of the exhaust gas, a dosing device for a reducing agent, an SCR catalytic converter, an oxidation catalytic converter and a diesel particle filter.

BACKGROUND OF THE INVENTION

The untreated exhaust gas of diesel engines contains, in addition to carbon monoxide CO, hydrocarbons HC and nitrogen oxides $NO_x$, a relatively high oxygen content of up to 15% by volume. Furthermore, said untreated exhaust gas contains particle emissions which are composed predominantly of soot residues and possibly organic agglomerates and which originate from a partially incomplete combustion of fuel in the cylinder.

To adhere to the legal exhaust-gas limit values for diesel vehicles which will be applicable in future in Europe, North America and Japan, the simultaneous removal of particles and nitrogen oxides from the exhaust gas is necessary. The pollutant gases carbon monoxide and hydrocarbons can easily be made harmless from the lean exhaust gas by oxidation on a suitable oxidation catalytic converter. Diesel particle filters with and without additional catalytically active coatings are suitable devices for the removal of the particle emissions. The reduction of the nitrogen oxides to form nitrogen ("denitrogenization" of the exhaust gas) is more difficult on account of the high oxygen content. One known method is the selective catalytic reduction (SCR) of the nitrogen oxides on a suitable catalytic converter, or SCR catalytic converter for short. Said method is currently preferred for the denitrogenization of diesel engine exhaust gases. The reduction of the nitrogen oxides contained in the exhaust gas takes place in the SCR process with the aid of a reducing agent which is dosed into the exhaust section from an external source. As reducing agent, use is preferably made of ammonia or of a compound which releases ammonia, such as for example urea or ammonium carbamate. The ammonia, which is possibly generated in situ from the precursor compound, reacts on the SCR catalytic converter with the nitrogen oxides from the exhaust gas in a comproportionation reaction to form nitrogen and water.

At present, in order to satisfy the upcoming legal regulations, a combination of the different exhaust-gas purification units is inevitable. A device for the purification of diesel engine exhaust gases must comprise at least one oxidation-active catalytic converter and, for denitrogenization, an SCR catalytic converter with an upstream device for introducing reducing agent (preferably ammonia or urea solution) and an external reducing agent source (for example an auxiliary tank with urea solution or an ammonia store). If it is not possible, by optimizing the engine-internal combustion, to keep the particle emissions sufficiently low that they can be removed by the oxidation catalytic converter by means of direct oxidation with oxygen, the use of a particle filter is additionally necessary.

Corresponding exhaust-gas purification systems have already been described; some are presently at the stage of practical testing.

For example, EP-B-1 054 722 describes a system for the treatment of $NO_x$ and particle-containing diesel exhaust gases, in which an oxidation catalytic converter is connected upstream of a particle filter. A reducing agent source and a dosing device for the reducing agent, and also an SCR catalytic converter, are arranged at the outflow side of the particle filter.

U.S. 2007/0044456 describes an exhaust-gas aftertreatment system which comprises, at the inflow side of a urea SCR catalytic converter (preferably transition metal/zeolite formulation with optimum $NO_x$ conversion in the temperature range between 200 and 500° C.), an oxidation catalytic converter (platinum-containing high-grade metal catalytic converter), and at the outflow side of the SCR catalytic converter, a diesel particle filter. A dosing device for urea is arranged between the oxidation catalytic converter and the SCR catalytic converter.

Both systems have in common that the untreated exhaust gas generated by the engine is conducted, in the first aftertreatment step, via an oxidation catalytic converter. The inventors have now established that such systems, which comprise an oxidation catalytic converter as the first exhaust-gas aftertreatment stage, are not suitable, without the inclusion of additional auxiliary measures, for purifying the exhaust gas of diesel engines of the most modern type, as are provided for example for EU-VI vehicles, to such an extent that the prescribed nitrogen oxide emission limit values can be adhered to.

SUMMARY OF THE INVENTION

It is an object of the present invention to provide an exhaust-gas purification system (method and device) by means of which the exhaust gas of diesel engines of the most modern type which have a charging turbine can be purified to such an extent that even the future legal emission limit values can be adhered to without additional auxiliary measures.

Said object is achieved by means of a method for the purification of exhaust gases which are generated by a diesel engine with a charging turbine and which, in addition to carbon monoxide, hydrocarbons and particles, contain nitrogen oxides with an $NO_2/NO_x$ ratio of between 0.3 and 0.7, with the exhaust gas being conducted via an SCR catalytic converter for the reduction of the nitrogen oxides to form nitrogen, via an oxidation catalytic converter for the oxidation of carbon monoxide and hydrocarbons to form $CO_2$, and through a diesel particle filter for the removal of particles. The method is characterized in that urea solution, or the solution of some other water-soluble compound which releases ammonia, is used as a reducing agent for the SCR reaction, which reducing agent is dosed into the exhaust section upstream of the charging turbine. To carry out the method according to the invention, a device for the purification of said exhaust gases is provided. Said device comprises, arranged in the flow direction of the exhaust gas, a dosing device for a reducing agent solution from a reducing agent reservoir, an SCR catalytic converter for the reduction of nitrogen oxides, an oxidation catalytic converter for the oxidation of carbon monoxide and hydrocarbons, and a diesel particle filter.

DETAILED DESCRIPTION OF THE INVENTION

The optimum $NO/NO_2$ ratio for the SCR catalytic converter is approximately 1 for all presently known SCR catalytic converters. Specified as the $NO_2/NO_x$ ratio, the optimum ratio lies between 0.3 and 0.7. Whether said ratio is obtained upstream of the SCR catalytic converter in a system according to EP-B-1 054 722 or according to U.S. 2007/0044456 is dependent on the exhaust-gas temperature and therefore on the operating state of the engine and on the activity of the oxidation catalytic converter. In the case of the system described in EP-B-1 054 722, the design and soot loading of the diesel particle filter which is connected downstream of the oxidation catalytic converter are further influential variables.

Figure 1:
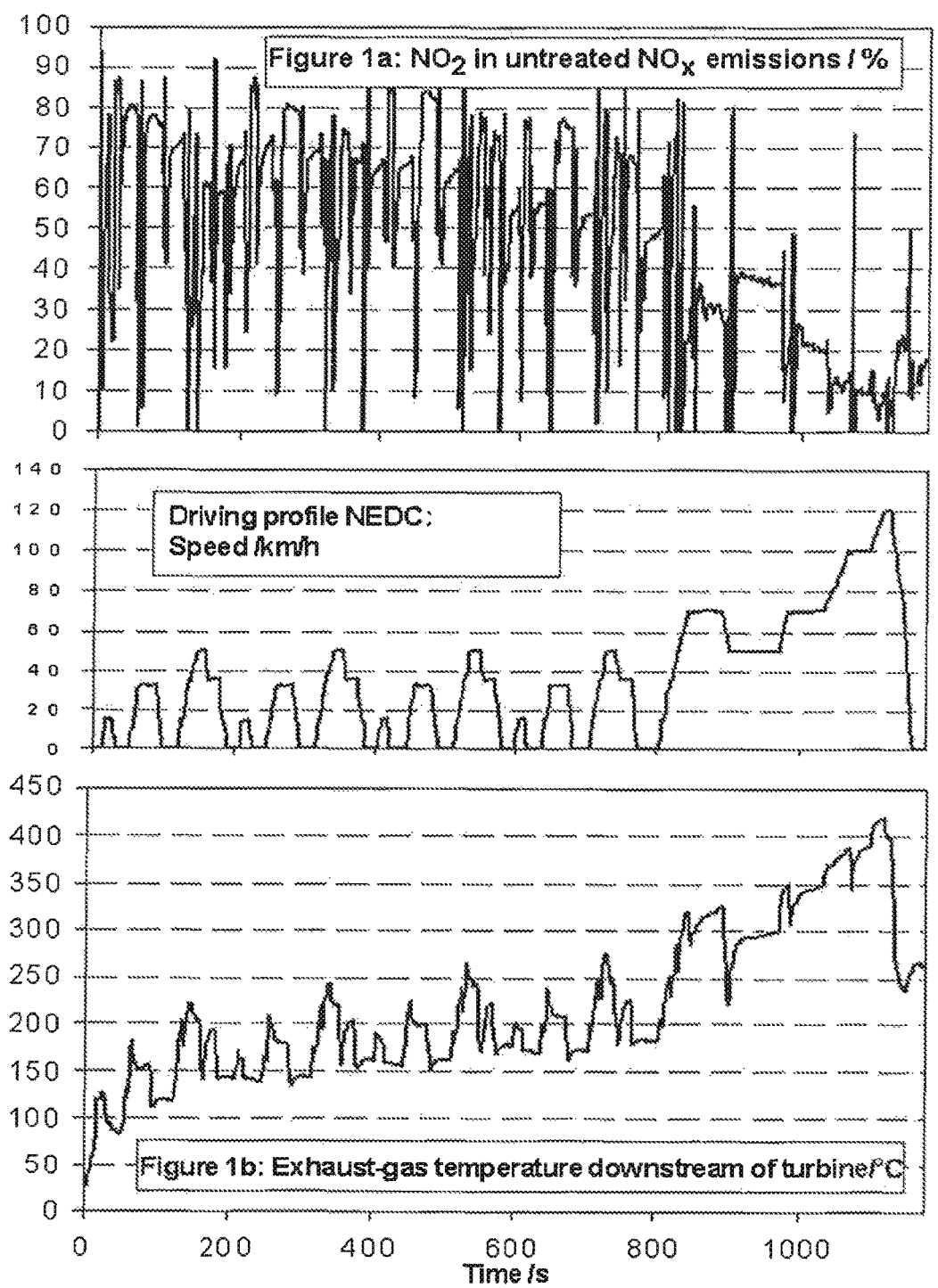
FIG. 1 illustrates: a) by way of example, the $NO_2$ proportion in the NO of the untreated emissions of a corresponding engine (4-cylinder common rail diesel engine, swept volume 2.2 l) in the European standard driving cycle, the New European Driving Cycle NEDC; and b) the associated exhaust-gas temperature profile.
Figure 2:
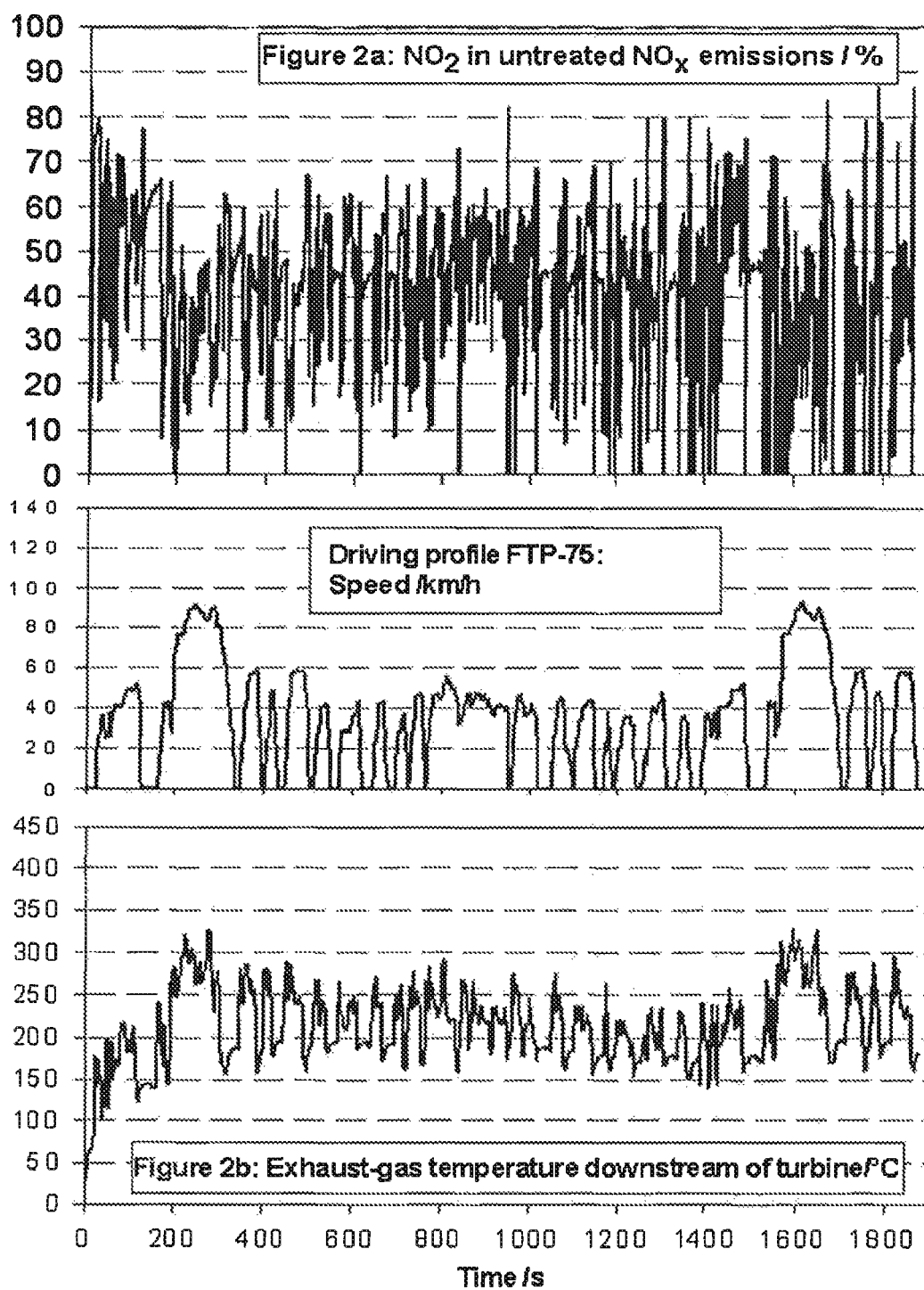
FIG. 2 shows the relevant emissions and exhaust-gas temperature data of the same engine as in FIG. 1, for operation in the North American standard driving cycle FTP-75, illustrating: a) $NO_2$ proportion in the untreated emissions; and b) exhaust-gas temperature level.

Diesel engines of the most modern type differ from the previously conventional diesel engines by a considerably higher exhaust-gas recirculation rate. This results in a rise in the $NO_2$ proportion in the $NO_x$ of the untreated emissions with a simultaneous considerable reduction in the mean exhaust-gas temperature. At many regular operating points, there is an $NO_2/NO_x$ ratio of 0.3 to 0.7. FIG. 1a shows, by way of example, the $NO_2$ proportion in the $NO_x$ of the untreated emissions of a corresponding engine (4-cylinder common rail diesel engine, swept volume 2.2 l) in the European standard driving cycle, the New European Driving Cycle NEDC; FIG. 1b shows the associated exhaust-gas temperature profile. FIG. 2 illustrates the relevant emissions and exhaust-gas temperature data of the same engine for operation in the North American standard driving cycle FTP-75 (a: $NO_2$ proportion in the untreated emissions; b: exhaust-gas temperature level).

Figure 3:
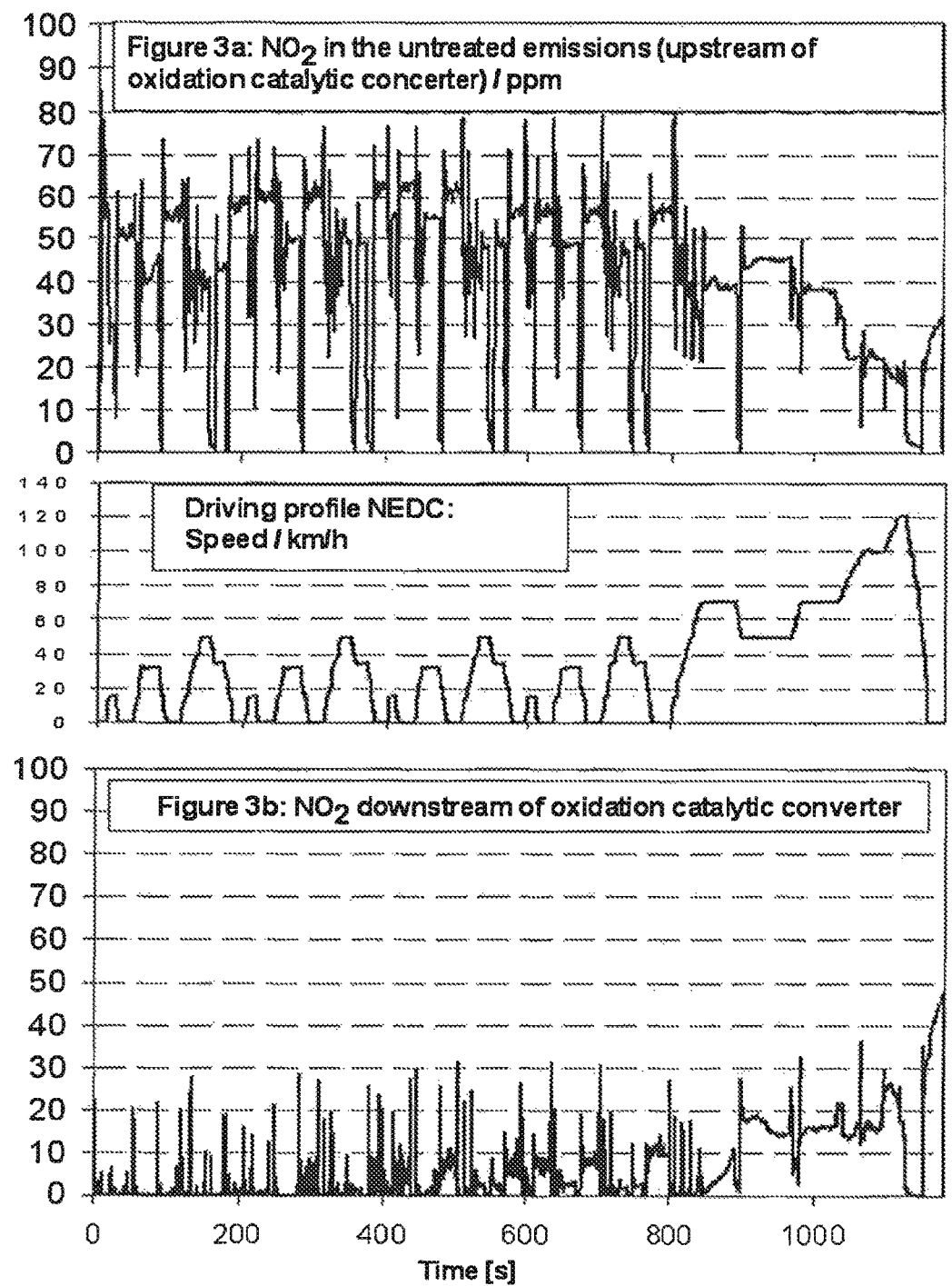
FIG. 3 shows a comparison of the $NO_2$ concentration in the exhaust gas of a diesel engine of the most modern type, at: a) a location upstream of the oxidation catalytic converter; and b) a location downstream of the oxidation catalytic converter.

The changed boundary conditions have the result that conducting the untreated exhaust gas of a diesel engine of the most modern type over an oxidation catalytic converter in the first exhaust-gas aftertreatment stage no longer leads, as described in EP-B-1 054 722, to an at least partial oxidation of NO to $NO_2$ and therefore to an increase in the $NO_2/NO_x$ ratio. The inventors have in fact found that, under the resulting operating conditions, the oxidation catalytic converter acts so as to deplete $NO_2$. FIG. 3 shows a comparison of the $NO_2$ concentration in the exhaust gas of a diesel engine of the most modern type upstream (FIG. 3a) and downstream (FIG. 3b) of the oxidation catalytic converter. It can be clearly seen that the $NO_2$ content is considerably reduced over the oxidation catalytic converter. Said $NO_2$ reduction is however not associated with a denitrogenization of the exhaust gas, that is to say with a significant reduction of the total $NO_x$ content in the exhaust gas. Since, as a result of the relatively low exhaust-gas temperature level, the $NO_2$ which is depleted across the oxidation catalytic converter can no longer be reproduced by oxidation over the SCR catalytic converter which, according to EP-B-1 054 722, is arranged at the end of the exhaust system, the downstream SCR catalytic converter no longer has an optimum denitrogenizing effect. Large $NO_x$ breakthroughs therefore often occur at low-load and part-load operating points; the future, more stringent nitrogen oxide emission limit values are exceeded.

In the exhaust-gas purification system according to the invention, the exhaust gas originating from a diesel engine with a charging turbine is firstly freed of nitrogen oxides in a targeted fashion by being conducted over an SCR catalytic converter. The exhaust gas of said new engines has, on average, a virtually optimum $NO_2/NO_x$ ratio of 0.3 to 0.7 for the SCR reaction, such that optimum denitrogenization rates can be obtained at all operating points of the engine, even at cold start and low-load points in which the exhaust-gas temperature lies below 200° C. Urea, or some other water-soluble compound which releases ammonia, is used as reducing agent in the SCR reaction. Said reducing agent solution is dosed into the exhaust section upstream of the charging turbine, such that the charging turbine can be used as a mixing element for homogenizing reducing agent and exhaust gas and the hydrolysis reaction of the reducing agent to form ammonia can be ensured at all operating points of the engine on account of the increased temperature level at said point, of at least 180° C.

As a result of said measures, effective denitrogenization performance in the first exhaust-gas aftertreatment stage of the system according to the invention is ensured. This, and the fact that the diesel particle filter is arranged at the end of the exhaust line and therefore at the coldest point, have the result that, in the system according to the invention, a passive regeneration of the diesel particle filter, which takes place upon the burning-off of soot, which takes place in situ, with $NO_2$ at temperatures above 280° C., is not assisted. Accordingly, in the event of a critical exhaust-gas counterpressure value being exceeded, the diesel particle filter must be actively regenerated. Here, the temperatures required for burning off the soot which has been deposited on the filter are generated by means of a post-injection of fuel into the exhaust section and a catalytic combustion of the fuel. In one preferred embodiment, the post-injection of fuel takes place at the inflow side of the SCR catalytic converter. The injected fuel is catalytically burned on the oxidation catalytic converter which is arranged at the outflow side of the SCR catalytic converter. The resulting exothermic reaction is sufficient to increase the temperature in the downstream diesel particle filter to values above the soot ignition temperature. In an alternative embodiment, the post-injection of fuel takes place between the oxidation catalytic converter and diesel particle filter. The catalytic combustion of the fuel may then for example take place on an oxidation-active catalytic coating which is applied to the diesel particle filter. Alternatively, a second oxidation catalytic converter may be connected directly upstream of the diesel particle filter, which second oxidation catalytic converter acts as a heating catalytic converter. The two latter embodiments have the advantage that the fuel quantity required for actively regenerating the particle filter need not be dragged as a hydrocarbon ballast across the SCR catalytic converter. The risk of contamination of the SCR catalytic converter is thereby considerably reduced. Furthermore, in such embodiments, both the catalytically active coating of the diesel particle filter and also the catalytically active coating of a heating catalytic converter which is possibly connected upstream may be optimally adapted to the requirements of the particle purification of the exhaust gas and the particle filter regeneration, without having to accept conflicting aims with other exhaust-gas purification requirements.

Figure 4:
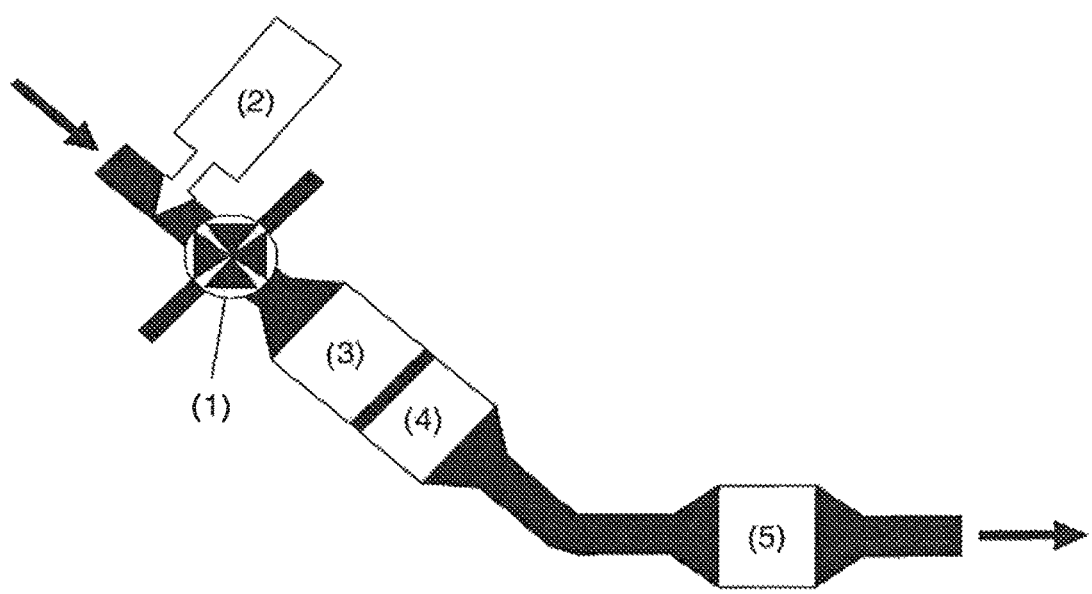
FIG. 4 shows a schematic illustration presenting one example of an exhaust gas purification device according to the present invention.

FIG. 4 shows a schematic illustration of a device according to claim 6 for carrying out the described method. The exhaust gas generated by the diesel engine of the most modern type, the flow direction of which exhaust gas is denoted by the arrows, comprises, in addition to the usual emissions of carbon monoxide, hydrocarbons and particles, nitrogen oxides with an $NO_2/NO_x$ ratio of between 0.3 and 0.7. Before the exhaust gas passes the charging turbine (1), a reducing agent solution from a reducing agent reservoir (2) is supplied to said exhaust gas by means of a dosing device. As a reducing agent solution, use is preferably made of urea solution, or the solution of some other water-soluble compound which releases ammonia, which is supplied from a corresponding tank by means of a conventional injection device. Upon passing the charging turbine, in addition to the hydrolysis of the reducing agent solution, a virtually complete homogenization of reducing agent and exhaust gas takes place. An SCR catalytic converter (3) is arranged at the outflow side of the charging turbine in a position close to the engine, which SCR catalytic converter (3) reduces the nitrogen oxides contained in the exhaust gas with the ammonia generated from the hydrolysis of the reducing agent solution, so as to form nitrogen. Only then are carbon monoxide (CO) and hydrocarbons (HC) made harmless, by means of oxidation to form carbon dioxide ($CO_2$), in an oxidation catalytic converter (4) which is arranged at the outflow side. Ammonia which is possibly still present in the exhaust gas, which ammonia was not consumed in the SCR catalytic converter, is likewise removed by oxidation in the oxidation catalytic converter. To keep temperature losses across the exhaust system as low as possible, and to thereby ensure the highest possible CO and HC conversion rates, the oxidation catalytic converter is preferably likewise arranged close to the engine, preferably in the same housing as the SCR catalytic converter (3). The exhaust gas which leaves said housing then contains only particles in addition to harmless constituents. Said exhaust gas flows onward to a diesel particle filter (5) which, for installation space reasons, is preferably arranged in the underbody region of the vehicle; as the exhaust gas passes through said diesel particle filter (5), the particles are filtered out, such that at the end of the system, exhaust gas which satisfies the legal requirements is discharged into the atmosphere.

To be able to operate the device according to the invention as effectively as possible and with high exhaust-gas purification efficiency, the selection of suitable catalytic converters is also of some significance in addition to the correct practical design.

The arrangement of the SCR catalytic converter close to the engine at the inflow-side end of the device therefore requires that the SCR catalytic converter which is used should have the highest possible resistance to contamination with regard to hydrocarbons in addition to sufficient resistance to thermal aging at temperatures of up to 800° C. Not all conventional SCR catalytic converter technologies can meet these demands. Conventional zeolitic SCR catalytic converters, as are described for example in U.S. Pat. No. 4,961,917, on account of their large zeolitic pore widths, have the tendency to accumulate hydrocarbons in the zeolitic framework, which leads to a blockage of ammonia storage locations and catalytic transition metal reaction centers which are essential for the functioning of said catalytic converters, and this can considerably reduce the activity of said catalytic converters. Conventional vanadium-pentoxide-based SCR catalytic converters usually do not have sufficient resistance to thermal aging.

In the device according to the invention, therefore, use is preferably made of cerium-oxide-based SCR technologies as are described for example in WO 2008/049491. Particularly preferable are SCR catalytic converters based on transition-metal-exchanged zeolite compounds or zeolite-like materials whose greatest lower duct width is between 2.6 and 4.2 angstrom (Å), and whose greatest lower duct width preferably does not exceed a value of 4.0±0.1 Å. SCR catalytic converters of said type preferably contain zeolites or zeolite-like materials from the group consisting of SAPO-34, ferrierite, SAPO-11, chabazite, erionite and mixtures thereof, which has a transition metal content of 0.1 to 10% by weight in relation to the weight of the zeolites or of the zeolite-like material, wherein the transition metal is particularly preferably selected from iron, copper and mixtures thereof.

For the oxidation catalytic converter which is arranged at the outflow side of the SCR catalytic converter, the installation position, which is conventionally characterized primarily by a colder exhaust-gas temperature than in devices according to the prior art, requires that the catalytic converter should have an ignition temperature (light-off temperature) for the oxidation of hydrocarbons and carbon monoxide of a maximum of 150° C. To meet said requirements, it is advantageous to use greater high-grade metal contents in the oxidation catalytic converter than in systems according to the prior art. Since, in the device according to the invention, the exhaust gas flowing through the oxidation catalytic converter has already been denitrogenized, it is possible to dispense with good NO conversion rates. It is thereby possible for possible increased costs, which would initially be expected as a result of the high-grade metal quantity which is to be increased overall, to be compensated in that, instead of the otherwise conventional high proportions of platinum, greater quantities of the cheaper palladium are used as a catalytically active component. An oxidation catalytic converter which is used in the device according to the invention preferably comprises between 0.35 and 7 grams per liter [g/L] of high-grade metal in relation to the catalytic converter volume, particularly preferably 3 to 5 g/L. The high-grade metal should be selected from the group consisting of platinum, palladium, rhodium, iridium, ruthenium and mixtures thereof. Platinum is preferably used in combination with palladium, but for cost reasons, not rhodium. The platinum:palladium ratio should lie between 10:1 and 1:5, preferably between 8:1 and 1:1, particularly preferably between 5:1 and 2:1.

To ensure good light-off behavior of the oxidation catalytic converter, it is advantageous if the oxidation catalytic converter is present in the form of a catalytic coating on a support body which warms up quickly. Such support bodies may for example include metallic honeycomb bodies or ceramic thin-walled honeycomb bodies (wall thickness: 0.06 to 0.1 millimeters) with standard cell densities (62 to 124 cells per square centimeter).

In the device according to the invention, as a diesel particle filter, use is preferably made of a catalytically coated wall-flow filter substrate composed of ceramic material or silicon carbide. The catalytic coating should be such that it firstly reduces the soot ignition temperature as effectively as possible, and secondly exhibits the lowest possible ignition temperature in the oxidation of hydrocarbons in order, during the active particle filter regeneration, to burn off unburned hydrocarbons, which are possibly present in the filter inlet, as quickly as possible and to thereby be able to contribute as effectively as possible to the generation of the exothermic reaction required for reaching the soot ignition temperature. For regular operation of the diesel particle filter between the active filter regeneration phases, it is also advantageous if the catalytic coating is such that hydrocarbons which possibly break through the oxidation catalytic converter, and nitrogen oxides which result from the over-oxidation of excess ammonia, can be converted with one another to form nitrogen, carbon dioxide and water (so-called HC-deNO$_x$ properties). To obtain said functionalities, the catalytically active coating preferably comprises 0.15 to 2 grams per liter [g/L] of high-grade metal selected from the group consisting of platinum, palladium and mixtures thereof, in relation to the volume of the diesel particle filter. 0.35 to 1 g/L of high-grade metal is particularly preferable.

By way of example, a device according to the invention may be fitted with the following:

an SCR catalytic converter, V=3.0 L, comprising a honeycomb body with a cell density of 62 cells per square centimeter and a cell wall thickness of 0.17 millimeters, which is provided with a catalytically active coating comprising a ferrierite-type zeolite which is exchanged with 5% by weight of copper and which has a lower duct width of a maximum of 4.2 Å;

an oxidation catalytic converter, V=2.0 L, comprising a ceramic honeycomb body with a cell density of 62 cells per square centimeter and a cell wall thickness of 0.1 millimeters, which is provided with a catalytically active coating which comprises 4 g/L of platinum and palladium, in the ratio 2:1, in relation to the volume of the oxidation catalytic converter, on a mixture of homogenous silicon-dioxide/aluminum-dioxide mixed oxide and γ aluminum oxide with an active surface of 200 m$^2$/g (BET); and a catalytically activated diesel particle filter with a volume of 4.0 L, comprising a ceramic wall-flow filter substrate with a cell density of 48 cells per square centimeter and a porosity of 50%, in the walls of which is placed a catalytically active coating which has a high-grade metal content of 0.9 g/L, in relation to the volume of the diesel particle filter, and a platinum:palladium ratio of 1:1.

The device according to the invention is suitable for the purification of the exhaust gases of diesel vehicles, in particular for the purification of the exhaust gases of diesel passenger vehicles, in which engines with a turbocharger (charging turbine) and an exhaust-gas recirculation device are used.

The invention claimed is:

1. A method for the purification of exhaust gases of a diesel engine that contain carbon monoxide, hydrocarbons, particles, and nitrogen oxides with an NO$_2$/NO$_x$ ratio of between 0.3 and 0.7, comprising:

performing the following steps, in the following flow sequence:

dosing, into an exhaust gas conducted through an exhaust section, at a location upstream of a charging turbine, a urea solution or a solution that is soluble to release ammonia for use as a reducing agent for an SCR reaction;

conducting the exhaust gas via an SCR catalytic converter for the reduction of nitrogen oxides to form nitrogen, the SCR catalytic converter comprising one or more transition-metal-exchanged zeolite compounds or zeolite-like materials with a greatest lower duct width of 2.6 to 4.2 angstrom;

conducting the exhaust gas via an oxidation catalytic converter for the oxidation of carbon monoxide and hydrocarbons to form CO$_2$; and conducting the exhaust gas through a diesel particle filter for the removal of particles.

2. The method as claimed in claim 1, wherein the charging turbine is used as a mixing element for homogenizing reducing agent and exhaust gas.

3. The method as claimed in claim 1, wherein the diesel particle filter is actively regenerated in the event of a critical exhaust-gas counterpressure value being exceeded, with the temperatures required for burning off the soot which has been deposited on the filter being generated by means of a post-injection of fuel into the exhaust section and a catalytic combustion of the fuel.

4. The method as claimed in claim 3, wherein the post-injection of fuel takes place at the inflow side of the SCR catalytic converter and the catalytic combustion of the fuel takes place on the oxidation catalytic converter which is arranged at the outflow side of the SCR catalytic converter.

5. The method as claimed in claim 1, wherein a post-injection of fuel takes place between the oxidation catalytic converter and diesel particle filter, and a catalytic combustion of the fuel takes place on an oxidation-active catalytic coating which is applied to the diesel particle filter, or on a second oxidation catalytic converter which is connected directly upstream of the diesel particle filter and which acts as a heating catalytic converter.

6. A device for the purification of exhaust gases which are generated by a diesel engine with a charging turbine and which, in addition to carbon monoxide, hydrocarbons and particles, contain nitrogen oxides with an NO$_2$/NO$_x$ ratio of between 0.3 and 0.7, comprising, arranged in the flow direction of the exhaust gas, a dosing device for dosing a reducing agent solution from a reducing agent reservoir, an SCR catalytic converter for the reduction of nitrogen oxides, the SCR catalytic converter comprising one or more transition-metal-exchanged zeolite compounds zeolite-like materials with a greatest lower duct width of 2.6 to 4.2 angstrom, an oxidation catalytic converter for the oxidation of carbon monoxide and hydrocarbons, and a diesel particle filter.

7. The device as claimed in claim 6, wherein the dosing device is arranged at the inflow side of the charging turbine.

8. The device as claimed in claim 6, wherein the reducing agent reservoir contains a urea solution, or a solution of some other water-soluble compound which releases ammonia.

9. The device as claimed in claim 6, wherein the SCR catalytic converter and oxidation catalytic converter are arranged in a position close to the engine and in the same housing.

10. The device as claimed in claim 6, wherein the oxidation catalytic converter is present in the form of a catalytic coating on a support body which warms up quickly, and said oxidation catalytic converter comprises 0.35 to 7 g/L of high-grade metal in relation to the catalytic converter volume, with the high-grade metal being selected from the group consisting of platinum, palladium, rhodium, iridium, ruthenium, and mixtures thereof.

11. The device as claimed in claim 10, wherein the high-grade metal comprises platinum in combination with palladium with a platinum: palladium ratio between 10:1 and 1:5.

12. The device as claimed in claim 6, wherein the diesel particle filter is a catalytically coated wall-flow filter substrate composed of ceramic material or silicon carbide, and the catalytically active coating comprises 0.15 to 2 g/L of high-grade metal selected from the group consisting of platinum, palladium, and mixtures thereof, in relation to the volume of the diesel particle filter.

13. A method of treating exhaust gas of a diesel engine, comprising:
conducting the exhaust gas via the device as claimed in claim 6.

* * * * *